United States Patent
Van Lancker

(10) Patent No.: US 7,141,666 B2
(45) Date of Patent: Nov. 28, 2006

(54) METHOD FOR PREPARING ALKALI AND HEAT STABLE POLYOLS

(75) Inventor: Frank Van Lancker, Aalst (BE)

(73) Assignee: Tate & Lyle Europe, Aalst (BE)

( * ) Notice: Subject to any disclaimer, the term of this patent is extended or adjusted under 35 U.S.C. 154(b) by 0 days.

(21) Appl. No.: 10/503,094

(22) PCT Filed: Dec. 31, 2002

(86) PCT No.: PCT/EP02/14898

§ 371 (c)(1),
(2), (4) Date: Sep. 10, 2004

(87) PCT Pub. No.: WO03/066553

PCT Pub. Date: Aug. 14, 2003

(65) Prior Publication Data

US 2005/0101777 A1    May 12, 2005

(30) Foreign Application Priority Data

Feb. 11, 2002    (BE) ................................ 2002/0080

(51) Int. Cl.
C07H 1/00     (2006.01)
C07C 35/14    (2006.01)

(52) U.S. Cl. ...................................... 536/124; 568/833

(58) Field of Classification Search ................ 536/124; 568/833

See application file for complete search history.

(56) References Cited

U.S. PATENT DOCUMENTS

| 3,040,104 A | 6/1962 | Sarappo et al. |
| 5,773,604 A | 6/1998 | Lefevre et al. |
| 6,417,346 B1 | 7/2002 | Salome et al. |

FOREIGN PATENT DOCUMENTS

| EP | 0262711 | 4/1988 |
| EP | 0711743 | 5/1996 |
| EP | 1095925 | 5/2001 |
| JP | 63/079844 | 4/1988 |

*Primary Examiner*—Shaojia Anna Jiang
*Assistant Examiner*—Everett White
(74) *Attorney, Agent, or Firm*—James Creighton Wray

(57) ABSTRACT

The invention relates to a method for preparing alkali and heat stable polyols, whereby sugar alcohols are treated with reagents to obtain stabilized sugar alcohol syrups and the stabilized alcohol syrup is subjected to a purification step by passing the stabilized sugar alcohol syrup over at least one ion-exchanger resin, and the stabilized sugar alcohol syrup being purified by a double passage over a cationic anionic ion-exchanger configuration (CACA), comprising at least a first weak acidic cationic ion-exchanger resin and a second strong, medium or weak basic anionic ion-exchanger resin.

17 Claims, 1 Drawing Sheet

METHOD FOR PREPARING ALKALI AND HEAT STABLE POLYOLS

This application claims the benefit of Belgian Application No. 2002/0080 filed Feb. 11, 2002 and PCT/EP02/14898 filed Dec. 31, 2002.

BACKGROUND OF THE INVENTION

The invention relates to a method for preparing alkali and heat stable polyols, in which sugar alcohols are treated with reagents to obtain a stabilized sugar alcohol syrup by means of reagents and the stabilized alcohol syrup is subjected to a purification stage by passing the stabilized sugar alcohol syrup over at least one ion-exchanger resin.

By polyols are meant sugar alcohol syrups, by which reference is made to the hydrogenation products of polysaccharide hydrolysates, comprising, but not restricted to, hydrolysates obtained from starch, xylanes, arabinoxylanes, cellulose or other vegetal polysaccharides. Typical starch hydrolysates are, for instance, dextrose, high DE glucose syrups, high maltose syrups, standard glucose syrups and maltodextrines, including low DE maltodextrines.

Alkali and heat stability or sugar alcohols is important in a number of industrial and food applications, as shown in JP 63/079644 and EP 0 711 743. The alkali and heat stability in these patent documents is obtained by treating sugar alcohols by means of reagents in such a manner that as much colour forming components as possible are removed.

In JP 63/079844 sugar alcohol syrups are treated at a pH=9.5–13 at high temperatures and during a period varying between 30 minutes and 2 hours.

In EP 0 711 743 stabilization is realized through a fermentation, oxidation or caramelisation stage.

The thus stabilized sugar alcohol syrup is then further subjected to a purification stage in order to obtain the final product.

In JP 63/079844 this purification stage comprises a treatment of the treated syrup with ion exchanger resins. Here the syrup, which was cooled down to 50° C. was first passed over a strong acid cationic resin, then over a weak or medium base anionic resin and finally over a mixed bed, composed of the same cationic and anionic resins as mentioned above and in a 1:2-ratio. The temperature at which these resins were used not being mentioned in this patent document.

In example 1 of EP 0 711 743, the stabilized syrup is purified by means of a strong acidic cationic resin and a strong basic anionic resin. Here also, no reference is made to any temperature at which these ion exchange resins are used.

In EP 1 095 925 an improved method is considered for purifying sugar alcohol syrups which were subjected to an alkali and heat stabilization treatment. In this method purification occurs by at least one passage of the stabilised sugar alcohol syrup over a strong acidic cationic resin at a temperature of below 50° C., in a preferred form of below 40° C. and in the most preferred form the temperature is situated between 20° C. and 30° C.

In EP 1 095 925 the importance of the working temperatures of resins with respect to the level of reducing sugars desired after purification is mentioned. From this it is apparent that working temperatures of below 30° C. give cause for products having an excellent heat and alkali stability, such as required for a number of applications.

The temperature is the more important when the hydrolysable sugar alcohol content of the syrup, for instance, maltitol, maltotriitol and hydrogenated oligosaccharides, increases.

From U.S. Pat. No. 5,254,174 the importance of the working temperature of strong acidic cationic resins with respect to the hydrolysis of the substrate treated, is considered. There, with respect to the oligosaccharide treatment, it is suggested to use the strong acidic cationic resins at temperatures situated between 25° C. and 35° C., in order to prevent hydrolysis of the oligosaccharides.

In U.S. Pat. No. 4,029,183 is considered how the inversion reaction of sucrose during decationization, is prevented by controlling the temperature of the strong acidic cationic resin between 25° C. and 30° C.

The use of strong acidic cationic resins during the refining of stabilised sugar alcohol syrups, however, has the disadvantage that, when products having a low reducing sugar content are needed, it is necessary to work at temperatures between 20° C. and 30° C. In order to cool down the syrups to these relatively low temperatures, additional cooling equipment and energy has to be used. As a consequence of these lower temperatures, the viscosity of these relatively concentrated syrups increases, because of which treatment is further complicated (pressure build-up in resins). This is more especially the case with syrups obtained through hydrogenation of, among others, starch hydrolysates that are mainly composed of di-, tri- and higher oligosaccharides (for instance, medium and high maltose syrups, maltodextrines). Another disadvantage of strong acidic resins is related to the fact that a large excess of acid is required in order to regenerate these resins.

In EP 0 262 711 the use of a combination of weak acidic cationic and weak or medium basic anionic resin is considered for purification of beet sugar thin juice.

It should be noted that this method aims at a partial demineralisation of beet sugar thin juice (as described in the examples). However, from these examples it becomes clear that the removal of cations and colour is far from complete.

SUMMARY OF THE INVENTION

The object of the invention is to provide for a method for preparing alkali and heat stable polyols not showing the disadvantages mentioned above.

This object is obtained by providing a method for preparing alkali and heat stable polyols, in which:

sugar alcohols are treated by means of reagents to yield a stabilized sugar alcohol syrup, and the stabilized sugar alcohol syrup is subjected to a purification stage by passing the stabilized sugar alcohol syrup over at least one ion-exchanger resin, and in which the stabilized sugar alcohol syrup is purified by means of a double passage over a cationic anionic ion-exchanger configuration (CACA), comprising at least a first weak acid cation ion-exchanger resin and a second strong, medium or weak base anion ion-exchanger resin.

In a preferred method according to the invention a temperature is used varying between 20° C. and 60° C.

In a preferred method, according to the invention, the CACA configuration uses a "merry-go-round" system, comprising at least 3 pairs of columns, each pair of columns consisting of a column filled with cationic ion-exchanger resin and a column filled with anionic ion-exchanger resin.

At least two pairs of columns are used for the purification of the stabilised sugar alcohol syrup, while at least a third pair of columns is regenerated.

Such a system has the advantage that the refining of the stabilised sugar alcohol syrup may be done in a continuous manner.

In a specific preferred method according to the invention said cationic ion-exchanger resin in the column is built-up of two layers, the layer of ion-exchanger resin at the exit of the column consisting of a strong acidic ion-exchanger resin.

In a more specific method according to the invention said strong acidic ion-exchanger resin represents 0.5% to 50% of the volume of the cationic ion-exchanger resin in the column.

In a still more specific method according to the invention said layer of strong acidic ion-exchanger resin represents 5% to 25% of the volume of the cationic resin in the column.

In a preferred method of the invention a temperature is used varying between 30° C. and 50° C.

In a specific preferred method according to the invention a temperature is used varying between 35° C. and 45° C.

In a particular method according to the invention the treatment of the sugar alcohols in order to obtain a stabilized sugar alcohol syrup, in a first stage comprises a hydrogenation of a corresponding polysaccharide hydrolysate to yield a hydrogenated sugar alcohol syrup, after which an alkali and heat treatment of the hydrogenated syrup is carried out in order to obtain said stabilized sugar alcohol syrup.

In a more particular method according to the invention the hydrogenating reaction is interrupted when the residual reducing sugars dry weight content drops below 0.2%.

In a most particular method according to the invention the hydrogenating reaction is interrupted when the residual reducing sugars dry weight content drops below 0.1%.

In an advantageous method according to the invention the conductivity of the refined sugar alcohol syrups amounts to less than 1% of the original conductivity.

In a more advantageous method according to the invention the conductivity of the refined sugar alcohol syrups amounts to less than 0.5% of the original conductivity.

Preferably, in the method according to the invention, sugar alcohols are used which, after hydrolysis, contain a total reducing sugar content, varying between 3.5% and 98%, as determined by means of Bertrand's method.

More preferably, in the method according to the invention, sugar alcohols are used which, after hydrolysis, contain a total reducing sugar content, varying between 40% and 95%, as determined by means of Bertrand's method.

Most preferably, in the method according to the invention, sugar alcohols are used which, after hydrolysis, contain a total reducing sugar content, varying between 50% and 92%, as determined by means of Bertrand's method.

In a preferred method according to the invention, said sugar alcohols are obtained by hydrogenation of medium to high maltose syrups.

The characteristics and particularities of the present invention are further explained hereafter on the basis of an implemented example, with reference to the drawing enclosed. It should be noted that specific aspects of this example are described as a preferred example only of what is meant in the scope of the general description of the invention mentioned above and on no account may be interpreted as a restriction of the scope of the invention as such and as expressed in the following claims.

BRIEF DESCRIPTION OF THE DRAWING

In the drawing enclosed.

DETAILED DESCRIPTION OF THE PREFERRED EMBODIMENTS

Figure 1:
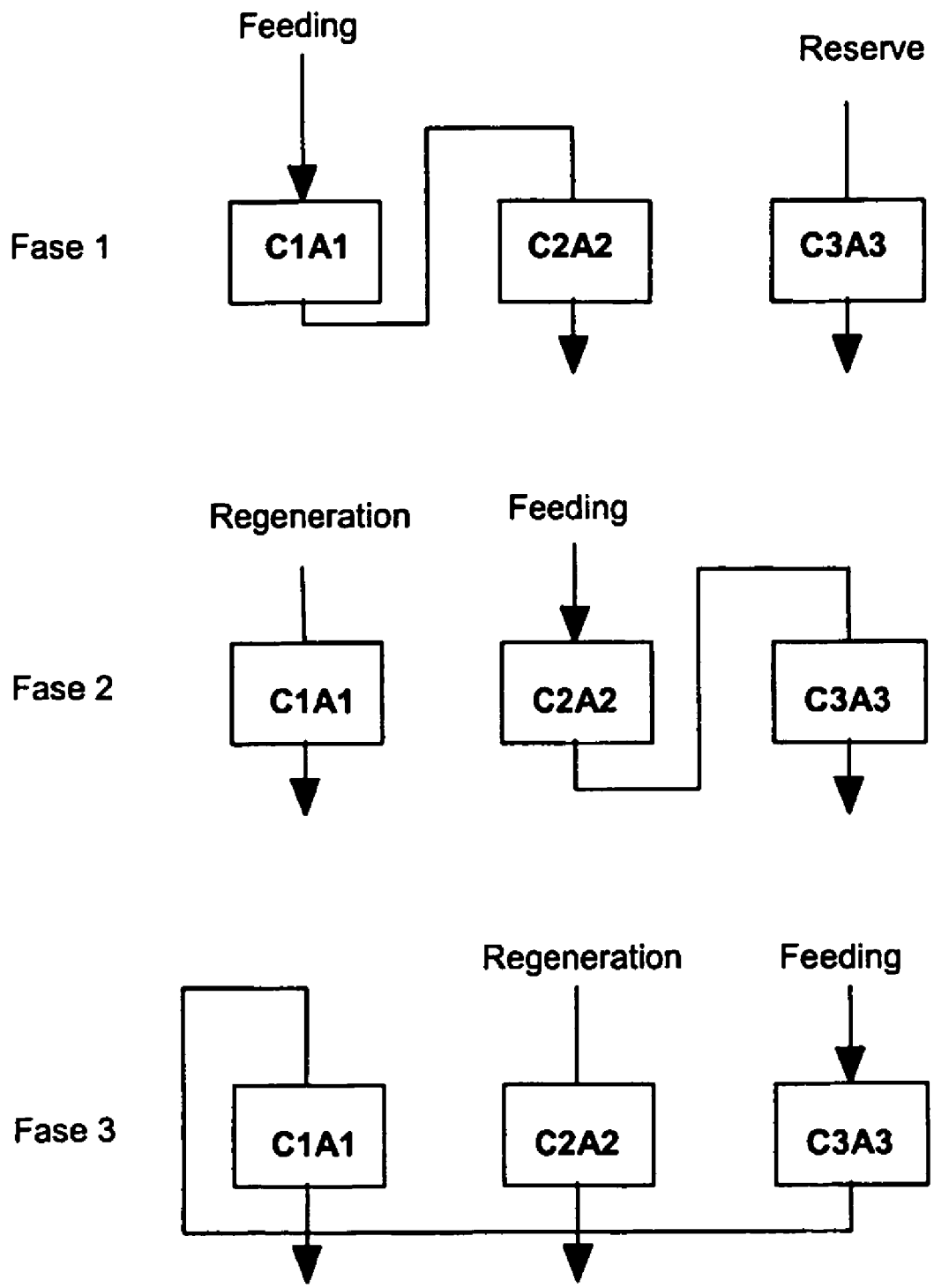
FIG. 1 is a schematic representation of a "merry-go-round" system according to the invention.

The method according to the invention, in a first stage comprises a hydrogenation of a corresponding polysaccharide hydrolysate (likewise called sugar alcohol), then an alkali and heat treatment of the hydrogenated sugar alcohol syrup in order to obtain a stabilized sugar alcohol syrup, and finally the purification or the refining of the stabilized sugar alcohol syrup, after which a sugar alcohol syrup is obtained which is alkali and heat resistant.

The method according to the invention is advantageous for sugar alcohol syrups containing a total reducing sugar content, after hydrolysis, varying between 3.5 and 98%, as determined by means of Bertrand's method. Further, it was also found, that this method also yields very good results when treating sugar alcohol syrups containing a total reducing sugar content, after hydrolysis, lying between 40% and 95%, preferably between 50 and 92%, as determined by means of Bertrand's method. Similar typical sugar alcohol syrups, such as mentioned above, are obtained through hydrogenation of medium to high maltose syrups.

The hydrogenation is carried out with the help of methods that are generally known in the state or the art. The hydrogenation is interrupted when the residual reducing sugar dry weight content drops below 0.2%, preferably below 0.1%.

The hydrogenated sugar alcohol syrup is then subjected to an alkali and heat treatment, in order to obtain a stabilised sugar alcohol syrup, the stabilised sugar alcohol syrup undergoing a colouration during this process.

In a next step, this stabilised sugar alcohol syrup is purified or refined, in order to remove the colour components present. The purification stage consists of a double passage (CACA) over a cationic anionic (CA) ion-exchanger configuration. In the process, use is made of a weak acidic cationic resin and a strong, medium or weak basic anionic resin, this at a temperature situated between 20° C. and 60° C., and in a still more preferred method the temperature varies between 30° C. and 50° C., and in a still more preferred method, between 35° C. and 45° C.

It is thereby of the utmost importance that after the CACA treatment the syrups are substantially entirely demineralised and colourless. Moreover, these syrups should remain substantially colourless, when subjected to an additional alkali and heat treatment.

In an advantageous method the CACA configuration is used in a "merry-go-round" system, as shown in FIG. 1. A similar system consists of 3 pairs of columns (or a plurality of them), each pair of columns consisting of a column filled with cationic resin and a column filled with anionic resin. Moreover two pairs of columns are used for purifying the treated syrup (CACA), while the third pair of columns is regenerated. The refined syrup is then collected after having passed the second set of CA-columns. Thus, when the first pair of columns gets exhausted, the supply is changed over to the second pair of columns and the refined syrup is then collected after the third set of CA-columns. At the same time the first set of resins is then sweetened off and regenerated.

In a variant of a method according to the invention, the cationic resin in the column is built-up of two layers, the layer of resin at the exit of the column consisting of a strong acidic cationic resin. This layer represents 0.5% to 50% of the volume of cationic resin, preferably between 5% and 25%.

After treatment, the conductivity of the refined sugar alcohol syrups amounts to less than 1%, preferably less than 0.5% of the original conductivity.

The sugar alcohol syrups obtained by means of the method according to the invention are most suitable for preparing products with an alkaline pH, or products containing an alkaline component, or which are treated or obtained through a heat treatment.

Hereafter, the invention will be further explained by means of a number of examples, which, however, should by no means be interpreted as a restriction of the scope of the invention as such and as expressed in the adjacent claims.

EXAMPLE 1

A high maltose syrup is hydrogenated according to standard procedures until the residual reducing sugar dry weight content is below 0.2%.

The hydrogenated syrup (about 50% d.w.), having a composition as indicated below, is then subjected to an alkali and heat treatment, the syrup being brought to a pH=11, and then heated during 2 hours at 100° C.

The composition of the syrup is as follows (dry weight %):

| | | |
|---|---|---|
| Sorbitol | 6.5% | |
| Maltitol | 62.5% | |
| Maltotriitol | 18.5% | |
| Higher DP polyols | 12.4% | |

After the alkaline heat treatment, the hydrogenated syrup is cooled down to a temperature situated between 35° C. and 40° C., and subjected to a purification step by means of ion-exchangers. The system is composed of three pairs of columns. Each pair consists of a column filled with a cationic resin and a column filled with an anionic resin.

The cationic resin used is a weak acidic cationic resin (Lewatit S8528) and the anionic resin is a strong basic resin (Lewatit OC1074). The resins are filled into double-walled glass columns having an internal diameter of 25 mm. The volume of the resin amounts to 100 ml of Lewatit S8528 and to 100 ml of Lewatit OC1704. The columns are heated to 35° C. and the velocity of flow is 200 ml/hour.

The supply to the first pair of columns was stopped after 3100 ml syrup had been treated by this first pair of columns (stage 1). Supply was then changed over to the second pair of columns, which before had been used as "finishing" pair.

The third pair of columns is now turned on as a "finishing" pair, while the first pair is sweetened off and regenerated (stage 2). Then the supply of this second pair of columns is stopped again after 3100 ml and supply is changed over to the third pair of columns (stage 3). In this manner operation continues in a "merry-go-round" configuration, always one pair of columns being regenerated, next to the CACA-refining system which is still operating. The refined syrup is collected at the exit of the second pair of columns of the CACA-configuration.

The extinction value of the non-refined substrate treated, before CACA-treatment, amounts to 4.25 (1 cm cuvette, 420 mm).

After CACA-treatment during the first stage, the syrup thus refined is subjected to an alkali and heat stability test. This test, called the S-test, is described in detail in EP711743. An increased stability of the sugar alcohol is reflected by low extinction values, as determined with this S-test (preferably <0,1).

The extinction value (S-value) of the sugar alcohol syrup mentioned above, after refining, was determined on the syrups collected during the first, second and third stage, as shown in FIG. 1.

| CACA-treatment | S-value |
|---|---|
| Stage 1 | 0.055 |
| Stage 2 | 0.052 |
| Stage 3 | 0.051 |

COMPARATIVE EXAMPLE 1

The malitol syrup of example 1 was subjected to an ion-exchanger purification stage, making use of the following combinations of resins:
(A) CA: strong acidic—medium basic (Dowex CM15 and Purolite A847S)
(B) CA: strong acidic—strong basic (Dowex CM15 and Lewatit OC1074)

Moreover, the purification stage was carried out at two different temperatures; 23° C. and 35° C.

In the table below, the S-values of the syrups thus treated are compared to the S-values of the products obtained by the method according to the invention.

| | Example 1 | (A)23° C. | (A)35° C. | (B)23° C. | (B)35° C. |
|---|---|---|---|---|---|
| S-value | 0.051 | 0.089 | 0.095 | 0.075 | 0.085 |

It may be concluded that the results obtained by the CACA-treatment according to the invention are permanently better than those obtained by the methods known already.

EXAMPLE 2

The maltitol syrup used in example 1 was subjected to an ion-exchanger purification stage, making use of a "merry-go-round" CACA-system, as described in example 1, the cationic resin in the column being composed of a layered bed of 90 ml weak acidic cationic resin (IMAC HP336) on top of a layer of 10 ml strong acidic cationic resin (Dowex CM15). The anionic resin is a medium basic resin (Purolite A847S).

The maltitol syrup of example 1 is refined over equal volumes of cationic and anionic resins at 35° C. The refined syrup has an S-value of 0.063.

The invention claimed is:
1. Method for preparing alkali and heat stable polyols, in which:
sugar alcohols are treated with reagents to obtain a stabilized sugar alcohol syrup, and
the stabilized sugar alcohol syrup is subjected to a purification stage by passing said stabilized sugar alcohol syrup over at least one ion-exchanger resin,
wherein the stabilized sugar alcohol syrup is purified by a double passage over an cationic anionic ion-exchanger configuration (CACA), comprising at least a first weak acidic cationic ion-exchanger resin and a second strong, medium or weak basic anionic ion-exchanger resin.

2. Method according to claim 1, wherein a temperature is used during the purification in the CACA system varying between 200° C. and 60° C.

3. Method according to claim 2, wherein a temperature is used which varies between 30° C and 50° C.

4. Method according to claim 2, wherein a temperature is used which varies between 35° C. and 45° C.

5. Method according to claim 1, wherein the CACA configuration uses a "merry-go-round" system, comprising at least 3 pairs of columns, each pair of columns consisting of a column filled with cationic ion-exchanger resin and a column filled with anionic ion-exchanger resin, and at least two pair of columns being used to purify the stabilized sugar alcohol syrup, while at least a third pair of columns is regenerated.

6. Method according to claim 5, wherein said cationic ion-exchanger resin in the column is built-up of two layers, the layer of ion-exchanger resin at the exit of the column consisting of a strong acidic ion-exchanger resin.

7. Method according to claim 6, wherein said layer of strong acidic ion-exchanger resin represents 0.5% to 50% of the volume of the cationic ion-exchanger resin in the column.

8. Method according to claim 7, wherein said layer of strong acidic ion-exchanger resin represents 5% to 25% of the volume of the cationic resin in the column.

9. Method according to claim 1, wherein the treatment of sugar alcohol in order to obtain a stabilized sugar alcohol syrup in a first stage comprises a hydrogenation of a corresponding polysaccharide hydrolysate to yield a hydrogenated sugar alcohol syrup, after which an alkali and heat treatment of the hydrogenated syrup is carried out in order to obtain said stabilized sugar alcohol syrup.

10. Method according to claim 9, wherein the hydrogenation reaction is interrupted when the residual reducing sugar dry weight content drops below 0.2%.

11. Method according to claim 9, wherein the hydrogenation reaction is interrupted when the residual reducing sugar dry weight content drops below 0.1%.

12. Method according to claim 1, wherein the conductivity of the refined sugar alcohol syrups is less than 1% of the original conductivity.

13. Method according to claim 1, wherein the conductivity of the refined sugar alcohol syrups is less than 0.5% of the original conductivity.

14. Method according to claim 1, wherein sugar alcohols are used which, after hydrolysis, contain a total reduced sugar content, varying between 3.5% and 98%, as determined by means of Bertrand's method.

15. Method according to claim 14, wherein sugar alcohols are obtained through hydrogenation of medium to high maltose syrups.

16. Method according to claim 1, wherein sugar alcohols are used which, after hydrolysis, contain a total reduced sugar content, varying between 40% and 95%, as determined by means of Bertrand's method.

17. Method according to claim 1, wherein sugar alcohols are used which, after hydrolysis, contain a total reduced sugar content, varying between 50% and 92%, as determined by means of Bertrand's method.

* * * * *